United States Patent
Son et al.

(10) Patent No.: US 10,047,099 B2
(45) Date of Patent: Aug. 14, 2018

(54) METHOD OF PRODUCING ANHYDROSUGAR ALCOHOL USING STEAM

(71) Applicant: SK Innovation Co., Ltd., Seoul (KR)

(72) Inventors: Sung Real Son, Daejeon (KR); Suk Joon Hong, Daejeon (KR); In Hyoup Song, Daejeon (KR); Yoon Jae Yim, Sejong-si (KR)

(73) Assignee: SK Innovation Co., Ltd., Seoul (KR)

( * ) Notice: Subject to any disclaimer, the term of this patent is extended or adjusted under 35 U.S.C. 154(b) by 55 days.

(21) Appl. No.: 15/247,030

(22) Filed: Aug. 25, 2016

(65) Prior Publication Data
US 2017/0057975 A1 Mar. 2, 2017

(30) Foreign Application Priority Data
Aug. 26, 2015 (KR) .................. 10-2015-0120483

(51) Int. Cl.
*C07D 493/04* (2006.01)
(52) U.S. Cl.
CPC ................. *C07D 493/04* (2013.01)
(58) Field of Classification Search
CPC .................................................. C07D 493/04
See application file for complete search history.

(56) References Cited

U.S. PATENT DOCUMENTS

| | | | |
|---|---|---|---|
| 6,639,067 B1 | 10/2003 | Brinegar et al. | |
| 7,615,652 B2 | 11/2009 | Holladay et al. | |

FOREIGN PATENT DOCUMENTS

| | | | | |
|---|---|---|---|---|
| KR | 101376481 B1 | 3/2014 | | |
| WO | WO 03089445 A2 * | 10/2003 | ........... | C07D 493/04 |
| WO | 2012081785 A1 | 6/2012 | | |

OTHER PUBLICATIONS

Bar, A., et al. "Sugar Alcohols." © 2012. Ullmann's Encyclopedia of Industrial Chemistry. Available from: < http://onlinelibrary.wiley.com/doi/10.1002/14356007.a25_413.pub3/pdf >.*
Fleche et al., "Isosorbide. Preparation, Properties and Chemistry", Lecture at the 36th Starch Convention of the Arbeitsgemeinschaft Getreideforschung at Delmod, Apr. 24-26, 1985, pp. 26-30.
Menegassi De Almeida et al., "Cellulose Conversion to Isosorbide in Molten Salt Hydrate Media", ChemSusChem, Feb. 2010, pp. 325-328, vol. 3.

\* cited by examiner

*Primary Examiner* — Noble E Jarrell
*Assistant Examiner* — John S Kenyon
(74) *Attorney, Agent, or Firm* — The Webb Law Firm

(57) ABSTRACT

The present invention provides a method for producing anhydrosugar alcohol, including: feeding sugar alcohol into a reactor and performing a dehydration reaction of the fed sugar alcohol to produce anhydrosugar alcohol; and supplying steam to the reactor to evaporate the produced anhydrosugar alcohol. According to the present invention, anhydrosugar alcohol can be produced in a high yield by increasing the specific surface area of reaction mother liquor and reducing the partial pressure of the product.

12 Claims, No Drawings

METHOD OF PRODUCING ANHYDROSUGAR ALCOHOL USING STEAM

CROSS-REFERENCE TO RELATED APPLICATION

This application claims priority to Korean Patent Application No. 10-2015-0120483 filed Aug. 26, 2015, the disclosure of which is hereby incorporated in its entirety by reference.

TECHNICAL FIELD

The present invention relates to a method for producing anhydrosugar alcohol using steam, and more particularly to a method for producing anhydrosugar alcohol using steam, in which high-temperature steam is injected into a reactor to increase the specific surface area of reaction mother liquor and reduce the partial pressure of anhydrosugar alcohol, thereby increasing the yield of anhydrosugar alcohol.

BACKGROUND ART

Due to the exhaustion of traditional energy sources together with an increase in the global energy demand, impetus is currently being given to the development of alternative energy sources. Among them, biomass is renewable biological resources that attract a great deal of attention.

Among biomass-based industrial raw materials, isosorbide ($C_6H_{10}O_4$) that is produced by dehydration of sorbitol ($C_6H_{14}O_6$) attracts attention as an environmentally friendly raw material for preparing polycarbonate (PC) as a substitute for bisphenol A (BPA), an epoxy monomer or an environmentally friendly plasticizer. Namely, isosorbide, a material that can be obtained by simple dehydration of sorbitol, is attracting attention as a monomer required for synthesis of next-generation, high-performance, environmentally friendly materials that can replace conventional polymer products, and many studies thereon have been conducted.

Environmentally friendly materials generally show poor properties compared to petrochemical-based materials, whereas isosorbide advantages in that it is environmentally friendly and, at the same time, shows excellent properties compared to conventional petrochemical-based materials. In addition, isosorbide may be used as an additive that can make plastic materials stronger and tougher, and isosorbide bonded to nitrate may also be used as an agent for treating cardiac diseases. When D-glucose obtained from biomass by pretreatment is hydrogenated in the presence of a catalyst, sorbitol is produced.

When D-glucose obtained from biomass by pretreatment is hydrogenated in the presence of a catalyst, sorbitol is produced. When one water molecule is removed from sorbitol, various sorbitans are produced, and when one water molecule is removed from some of these sorbitan isomers, isosorbide is produced. The sorbitan isomers that are converted to isosorbide are 1,4-sorbitan and 3,6-sorbitan, and the major isomers that cannot be converted to isosorbide are 2,5-sorbitan and 1,5-sorbitan. In the dehydration reaction process in which sorbitan is produced from sorbitol, 1,4-sorbitan is produced within a short time at a relatively low temperature (120 to 150° C.), and 2,5-sorbitan is produced over a long time at a temperature higher than 1,4-sorbitan. Other sorbitan isomers are produced at relatively low rates. A double dehydration reaction that produces isosorbide is influenced by various reaction conditions, including temperature, pressure, solvent, catalyst, etc. Sorbitans that are mainly produced from the single dehydration reaction of sorbitol are 1,4-sorbitan and 2,5-sorbitan. Thus, in order to increase the yield of isosorbide, the conditions of the control should be controlled such that the promotion of 1,4-sorbitan is promoted and the production of 2,5-sorbitan is suppressed.

Currently, as a method of preparing isosorbide from sorbitol, a process is widely used in which sulfuric acid is used as a catalyst and a reaction is carried out under a reduced pressure of about 10 mmHg. However, because isosorbide has a high boiling point and is easily degraded or denatured by heat at high temperatures, it is difficult to separate isosorbide by general atmospheric pressure distillation. For this reason, isosorbide is separated by distilling the reaction product at a relatively low temperature of about 150-220° C. under a vacuum of about 1-10 mmHg.

Methods of separating isosorbide in the presence of acid catalysts under vacuum conditions as described above have been disclosed.

U.S. Pat. No. 6,639,067 discloses a process comprising: dehydrating sugar alcohol by a direct heating method in the presence of an acid catalyst and an organic solvent to form a product which is soluble in the organic solvent; and then separating water, the organic solvent and the reaction by evaporation, distillation, recrystallization or extraction, and recycling the organic solvent.

Korean Patent No. 1376481 discloses a method for producing isosorbide, which comprises dehydrating sorbitol in the presence of a solid acid catalyst to produce isosorbide and separating the produced isosorbide by distillation.

However, the prior art patents as described above have problems in that a temperature of 170° C. or higher is required to evaporate isosorbide at a pressure of about 10 mmHg and in that when the produced isosorbide stays in the reactor for a long time without being evaporated, it is modified into other substances. In other words, even though a high temperature of 170° C. is maintained at the above pressure, isosorbide can be evaporated only when it is rapidly released from the surface of the reaction mother liquor.

Thus, the temperature at which the production of 1,4-sorbitan is promoted is preferably 100 to 150° C., whereas a temperature of 170° C. or higher is required to separate the produced isosorbide by distillation. For this reason, an operating method capable of all these requirements is required.

Accordingly, the present inventors have found that, when steam is injected as an assistant material for increasing the specific surface area of a reaction mother liquor in a vacuum reaction that converts sorbitol into isosorbide, the specific surface area of the mother liquor can be increased and the partial pressure of the product and the reaction time can be reduced, and as a result, isosorbide can be produced in a high yield, thereby completing the present invention.

SUMMARY OF INVENTION

It is an object of the present invention to provide a method for producing anhydrosugar alcohol, which can increase the yield of anhydrosugar alcohol in a vacuum reaction that converts sugar alcohol into anhydrosugar alcohol by dehydration.

To achieve the above object, the present invention provides a method for producing anhydrosugar alcohol, comprising the steps of: (a) feeding sugar alcohol into a reactor and performing a dehydration reaction of the fed sugar alcohol to produce anhydrosugar alcohol; (b) supplying steam to the reactor to evaporate the produced anhydrosugar alcohol; and (c) condensing and separating the evaporated anhydrosugar alcohol vapor and the steam, thereby recovering liquid anhydrosugar alcohol.

DETAILED DESCRIPTION OF THE INVENTION

Unless defined otherwise, all technical and scientific terms used herein have the same meaning as commonly understood by one of ordinary skill in the art to which the invention pertains. Generally, the nomenclature used herein and the experiment methods, which will be described below, are those well-known and commonly employed in the art.

In the present invention, it was found that, when high-temperature steam effective as an assistant material for increasing the specific surface area of a reaction mother liquid is injected in order to rapidly release and evaporate isosorbide from the surface of the reaction mother liquor in a vacuum reaction that converts sugar alcohol to anhydrosugar alcohol by dehydration, it can increase the temperature of the reaction mother liquor so that the formation and rapid evaporation of isosorbide can occur, thereby increasing the yield of isosorbide.

Therefore, in one aspect, the present invention is directed to a method for producing anhydrosugar alcohol, comprising the steps of: (a) feeding sugar alcohol into a reactor and performing a dehydration reaction of the fed sugar alcohol to produce anhydrosugar alcohol; (b) supplying steam to the reactor to evaporate the produced anhydrosugar alcohol; and (c) condensing and separating the evaporated anhydrosugar alcohol vapor and the steam, thereby recovering liquid anhydrosugar alcohol.

A temperature of 170° C. or higher is required to evaporate isosorbide at a pressure of about 10 mmHg, and when the produced isosorbide stays in the reactor for a long time without being evaporated, it is modified into other substances. In other words, even though a high temperature of 170° C. is maintained at the above pressure, isosorbide can be evaporated only when it is rapidly released from the surface of the reaction mother liquor. For this, an assistant material for increasing the specific surface area of the reaction mother liquor may be added to the reaction mother liquor in order to promote evaporation of the produced isosorbide. Consequently, in the present invention, steam is injected in order to increase the specific surface area of the mother liquor.

In the present invention, the dehydration reaction of sorbitol is performed at a pressure of 5-200 mmHg, preferably 10-120 mmHg, and a temperature of 120 to 150° C. for 50-150 minutes, preferably 50-90 minutes, so that the yield of 1,4-sorbitane can be maximized.

Next, steam having a temperature of 150 to 280° C. is injected into the reactor to increase the temperature of the reaction solution so that the formation and rapid evaporation of isosorbide can occur. That is, the high-temperature steam serves as an assistant material to increase the reaction temperature and assist in evaporation of isosorbide.

The steam may be injected in an amount of 0.01-30 wt %/min, preferably 0.1-10 wt %/min, based on the weight of the sugar alcohol.

As the amount of steam injected increases, the above-described effect is increased. However, if the amount of steam injected is excessively large, it will increase the operating cost and also increase the volume of reactant plus steam in the reactor to increase the size of the reactor to thereby increase equipment investment. For this reason, the amount of steam used is determined considering these facts.

The evaporated isosorbide vapor and the steam may be condensed in a condenser to form a liquid which is then recovered. The condenser may be maintained at a temperature of −40 to 100° C. The isosorbide product obtained as described above has a purity of 80-98% on a dry weight basis, and is obtained in a yield higher than those produced by conventional direct high-temperature distillation methods.

The steam is preferably injected through a sparger into the reactor so that it can be maximally mixed with the reaction mother liquor. If the reactor has a separate stirrer installed therein, the effect of increasing the yield of isosorbide can further be increased.

In addition, if the reaction temperature in the vacuum reaction that converts sugar alcohol to anhydrosugar alcohol is controlled to two steps of temperature, the yield of anhydrous sugar can further be increased.

In the present invention, the sugar alcohol may be hexitol. Specifically, it may be one or more selected from the group consisting of sorbitol, mannitol and iditol. Preferably, it is sorbitol. The anhydrosugar alcohol may be isosorbide, isomannide, isoidide or the like. Preferably, the anhydrosugar alcohol is isosorbide.

The method for producing anhydrosugar alcohol according to the present invention may be performed in a continuous or batch manner. It may be performed in a continuous stirred tank reactor (CSTR), a plug flow reactor (PFR), a trickle bed reactor (TBR) or a batch reactor (BR).

Preferably, an aqueous solution of sugar alcohol may be subjected to a first-step reaction at a temperature of 100 to 150° C. in the presence of a catalyst, and then subjected to a second-step reaction at a temperature of 151 to 240° C.

Sorbitol and the catalyst are fed into the first-step reactor and reacted at a temperature of 1-200 mmHg, preferably 3-100 mmHg, more preferably 5-40 mmHg, and a temperature of 100-150° C., so that the selectivity for 1,4-sorbitan is maximized. The residence time (reaction time) in the reactor is 10-300 minutes so that the conversion of sorbitol to isosorbide is 50% or more, preferably 75% or more.

The reaction solution in the first-step reactor is continuously fed into and reacted in a second-step reactor which is maintained at a temperature of 151 to 240° C., so that the produced isosorbide can be evaporated in the reactor after production. The reaction in the second-step reactor is performed at a pressure of 1-200 mmHg, preferably 3-100 mmHg, more preferably 5-40 mmHg, and a temperature of 151 to 240° C., and the residence time in the second-step reactor is 10-180 minutes.

The temperature of the first-step reaction may preferably range from 100° C. to 150° C., and the temperature of the second-step reaction may range from 151° C. to 240° C. In this temperature range, the effect of increasing the yield of isosorbide is obtained. In addition, the temperature difference between the first-step reaction and the second-step reaction is preferably 50° C. to 120° C.

If the temperature of the first-step reaction is lower than 100° C., the reaction time or the residence time will be very long, and if the temperature of the first-step reaction is higher than 150° C., side reactions can be promoted to reduce the yield of isosorbide. Meanwhile, if the temperature of the second-step reaction is lower than 151° C., the reaction for the conversion of 1,4-sorbitan to isosorbide will not be sufficiently performed, and if the temperature of the second-step reaction is higher than 240° C., side reactions in which 1,4-sorbitan or the produced isosorbide is degraded, modified or polymerized will strongly occur so that the yield of isosorbide can decrease rather than increase.

In the present invention, the time of the first-step reaction may be 10-300 minutes, and the time of the second-step reaction may be 10-180 minutes. In the first-step reaction, sorbitol is allowed to react in the forward direction at a low temperature without producing by-products, and in the second-step reaction, the product of the first-step reaction is exposed to a high temperature for a short time so that it will not produce other by-products. Thus, the first-step reaction may be performed for the time during which the starting material sorbitol is completely converted, and the second-step reaction may be performed for the time during which a sufficient amount of isosorbide can be evaporated.

In addition, the method for producing anhydrosugar alcohol according to the present invention may further comprise, after producing the anhydrosugar alcohol, a step of separating and/or purifying the product. The step of separating and/or purifying the product may be performed using distillation, crystallization and adsorption processes alone or in combination of two or more.

EXAMPLES

Hereinafter, the present invention will be described in further detail with reference to examples. It will be obvious to a person having ordinary skill in the art that these examples are illustrative purposes only and are not to be construed to limit the scope of the present invention. Thus, the substantial scope of the present invention will be defined by the appended claims and equivalents thereof.

Example 1

1000 g of D-sorbitol (Aldrich) was fed into a 1000-mL reactor and heated to a reaction temperature of 173° C. so as to be dissolved, and then 0.5 wt % of naphthalenesulfonic acid hydrate (Aldrich) was added thereto. Then, steam having a temperature of 180 to 250° C. was injected into the reactor at a rate of 0.3 wt %/min with stirring, and the pressure in the reactor was reduced to 5-10 mmHg. After 1 hour of the reaction, the formed reaction product was diluted 20-fold with water and analyzed by high-performance liquid chromatography (HPLC, Agilent; equipped with a carbohydrate column).

Examples 2 and 3 and Comparative Examples 1 and 2

The process of Example 1 was repeated, except that the amount of steam injected, the temperature and other conditions were changed as shown in Table 1 below.

TABLE 1

| No. | Steam injection rate* [wt %/min] | Temperature [° C.] | Other conditions |
|---|---|---|---|
| Comp.Ex. 1 | None | 173 | |
| Comp.Ex. 2 | None | 194 | |
| Example 1 | 0.3 | 173 | |

TABLE 1-continued

| No. | Steam injection rate* [wt %/min] | Temperature [° C.] | Other conditions |
|---|---|---|---|
| Example 2 | 0.3 | 194 | |
| Example 3 | 0.6 | 173 | |
| Example 4 | 0.3 | 130 → 170 | Sorbitol 500 g |

*the amount of steam injected based on the weight of sorbitol fed.

In addition to the above-described conditions, the following common conditions were used unless indicated otherwise:

pressure: 5-10 mmHg steam temperature: 180 to 250° C.

amount of sorbitol fed: 1,000 g catalyst: 0.5 wt % of naphthalenesulfonic acid hydrate.

The yields of the products obtained in Examples 1 to 3 and Comparative Examples 1 and 2 are shown in Tables 2 to 4 below.

TABLE 2

| No. | Amount of ISB remaining in distillate [wt %] | Amount of ISB remaining in residue [wt %] | Total amount of ISB [wt %] | Reaction time [h] |
|---|---|---|---|---|
| Comp.Ex.1 | 45.60 | 8.29 | 53.89 | 5 |
| Comp.Ex.2 | 53.95 | 1.08 | 55.02 | 4 |
| Example 1 | 53.56 | 2.72 | 56.28 | 5 |
| Example 2 | 55.24 | 0.24 | 55.48 | 4 |

As can be seen in Table 2 above, in the cases in which steam was injected at the same temperature for the same time, the yield of isosorbide was higher in Example 1 (performed at a temperature of 173° C.) than in Comparative Example 1 (performed at a temperature of 173° C.) and higher in Example 2 (performed at a temperature of 194° C.) than in Comparative Example 2 (performed at a temperature of 194° C.). The amount of isosorbide in the residue was also significantly reduced by the stripping effect of steam.

TABLE 3

| No. | Amount of ISB remaining in distillate [wt %] | Amount of ISB remaining in residue [wt %] | Total amount of ISB [wt %] | Reaction time [h] |
|---|---|---|---|---|
| Comp.Ex.1 | 45.60 | 8.29 | 53.89 | 5 |
| Example 3 | 52.49 | 6.44 | 58.92 | 3.5 |

As can be seen in Table 3 above, in the cases in which steam was injected at the same temperature, the yield of isosorbide was higher in Example 3 (in which the residence time in the reactor was shorter than that in Comparative Example 1) than in Comparative Example 1.

TABLE 4

| No. | Amount of ISB remaining in distillate [wt %] | Amount of ISB remaining in residue [wt %] | Total amount of ISB [wt %] | Reaction time [h] |
|---|---|---|---|---|
| Comp.Ex.1 | 45.60 | 8.29 | 53.89 | 5 |
| Example 4 | 59.62 | 0.22 | 59.85 | 6* |

*130° C. for 3 hrs → 170° C. for 3 hrs.

In the case in which the reaction temperature was changed in two steps and steam was injected in the higher-temperature step (Example 4), the yield of isosorbide in Example 4 was 30% higher than that in Comparative Example 1, and this increase in the yield was significant.

Example 5: Steam Feed Simulation

Using Aspen plus V8.2 program, the effect of steam injection on the evaporation of isosorbide produced by a reaction was evaluated based on the reduction in the partial pressure of the product in the reactor.

The amount of steam used is defined as the wt % of steam/feed.

The change in the partial pressure is defined as follows:

partial pressure (ISB, w/o stripping)=partial pressure (ISB, w stripping)/partial pressure (ISB, w/o stripping)

When steam was used in an amount equivalent to about 10-3000 of the feed, the partial pressure of ISB in the reactor was 26-91.6% reduced.

Example 6: Steam Injection Simulation

When steam was used in an amount equivalent to about 20-250% of the feed, the partial pressure of ISB in the reactor was 41-90% reduced.

Example 7: Steam Injection Simulation

When steam was used in an amount equivalent to about 30-200% of the feed, the partial pressure of ISB in the reactor was 52-87.9% reduced.

As confirmed in Examples 5 to 7, when steam was injected in the process for producing anhydrosugar alcohol according to the present invention, the partial pressure of the product in the reactor was reduced, and thus isosorbide produced by the reaction was effectively evaporated.

INDUSTRIAL APPLICABILITY

As described above, in the method for producing anhydrosugar alcohol according to the present invention, the total yield of the final product isosorbide can be increased by increasing the specific surface area of the reaction mother liquor and reducing the partial pressure of the product to increase the efficiency of evaporation of the product.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A method of producing anhydrosugar alcohol, comprising:
   (a) feeding sugar alcohol into a reactor and performing a dehydration reaction of the sugar alcohol to produce anhydrosugar alcohol;
   (b) supplying steam at a temperature of 150 to 280° C. into the reactor to evaporate the anhydrosugar alcohol; and
   (c) condensing and separating the evaporated anhydrosugar alcohol vapor and the steam, thereby recovering liquid anhydrosugar alcohol,
   wherein the anhydrosugar alcohol is one or more selected from the group consisting of isosorbide, isomannide and isoidide and the sugar alcohol is one or more selected from the group consisting of sorbitol, mannitol and iditol.

2. The method of claim 1, wherein the dehydration reaction is performed at a pressure of 5-200 mmHg and a temperature of 120 to 150° C. for 50-150 minutes.

3. The method of claim 1, wherein the steam is supplied in an amount of 0.01-30 wt %/min, based on a weight of the sugar alcohol.

4. The method of claim 3, wherein the steam is supplied in an amount of 0.1-10 wt %/min, based on the weight of the sugar alcohol.

5. The method of claim 1, wherein the steam is supplied to the reactor through a sparger.

6. The method of claim 1, wherein the reactor comprises a stirrer installed therein for mixing the steam supplied to the reactor.

7. The method of claim 1, wherein the anhydrosugar alcohol is isosorbide, and the sugar alcohol is sorbitol.

8. The method of claim 1, wherein the dehydration reaction is performed by subjecting an aqueous solution of sugar alcohol to a first-step reaction at a temperature of 100 to 150° C. in the presence of a homogeneous catalyst, and then subjecting the aqueous solution of sugar alcohol to a second-step reaction at a temperature of 151 to 240° C.

9. The method of claim 8, wherein the first-step reaction and the second-step reaction are performed at a pressure of 1-200 mmHg.

10. The method of claim 8, wherein the first-step reaction and the second-step reaction are performed for a reaction time of 10-300 minutes and 10-180 minutes, respectively.

11. The method of claim 1, which is performed in a continuous stirred tank reactor (CSTR), a plug flow reactor (PFR), a trickle bed reactor (TBR) or a batch reactor (BR).

12. The method of claim 8, wherein the second-step reaction product is collected by being condensed to liquid in a condenser maintained at a temperature of −40 to 100° C.

* * * * *